United States Patent
Elliott

(10) Patent No.: US 8,178,854 B1
(45) Date of Patent: May 15, 2012

(54) GERMICIDAL CIGAR HUMIDIFIER

(76) Inventor: Richard Eugene Elliott, Norton, MA (US)

( * ) Notice: Subject to any disclaimer, the term of this patent is extended or adjusted under 35 U.S.C. 154(b) by 0 days.

(21) Appl. No.: 13/094,461

(22) Filed: Apr. 26, 2011

(51) Int. Cl.
*A61L 2/00* (2006.01)
*G01N 21/00* (2006.01)
*A61N 5/00* (2006.01)
*A24F 13/24* (2006.01)
*A24F 13/00* (2006.01)
*A24F 25/00* (2006.01)
*A24B 27/00* (2006.01)
*A24F 15/00* (2006.01)

(52) U.S. Cl. ......... 250/492.1; 422/22; 422/24; 422/307; 250/454.11; 250/455.11; 131/329; 131/328; 131/250; 131/121; 312/31; 312/231; 206/85; 206/242; 206/514

(58) Field of Classification Search ............... 422/22, 422/24, 307; 250/454.11, 455.11, 492.1; 131/329, 328, 250, 121; 312/31, 231; 206/85, 206/242, 514
See application file for complete search history.

(56) References Cited

U.S. PATENT DOCUMENTS

| 1,481,325 A | * | 1/1924 | Le Gris | 239/55 |
| 3,852,032 A | * | 12/1974 | Urbach | 422/24 |
| 3,955,922 A | * | 5/1976 | Moulthrop | 422/300 |

* cited by examiner

*Primary Examiner* — Jill Warden
*Assistant Examiner* — Monzer Chorbaji
(74) *Attorney, Agent, or Firm* — Michael D. Eisenberg

(57) ABSTRACT

The present invention relates to a cigar humidor, comprising: a hollow housing; a lid connected to the housing; a germicidal light assembly positioned inside the housing for disinfecting cigars; and a platform transparent to ultraviolet light produced by the assembly.

6 Claims, 4 Drawing Sheets

GERMICIDAL CIGAR HUMIDIFIER

TECHNICAL FIELD

The present invention, in some embodiments thereof, relates to cigar humidifiers.

BACKGROUND OF THE INVENTION

Cigars are made of a tightly-rolled bundle of dried and fermented tobacco. Because of their composition, and being ideal stored in a humid environment to prevent from drying out, there is opportunity for fungus to proliferate. The present invention addresses the need for a cigar humidifier that kills and impedes the growth of fungus stored in a humidifier.

BRIEF SUMMARY OF EMBODIMENTS OF THE INVENTION

The present invention relates to a cigar humidor, comprising: a hollow housing; a lid connected to the housing; a germicidal light assembly positioned inside the housing for disinfecting cigars; and a platform transparent to ultraviolet light produced by the assembly.

In a variant, the cigar humidor comprises a mirror positioned against an inside surface of the lid configured to face inside the hollow housing of the humidor when the lid is closed. The minor is configured to reflect light emitted by the germicidal light assembly, toward cigars placed on the platform.

In another variant the cigar humidor comprises a temperature sensor configured to measure the air temperature inside the humidor and a controller in electrical communication with the temperature sensor and configured to operate the germicidal light assembly according to a predetermined temperature set point.

In a further variant of the cigar humidor, the controller is configured to operate the germicidal light assembly according to a predetermined time sequence.

In yet another variant, the predetermined time sequence comprises a repeating cycle of operating the light on for two hours followed by shutting off the light for one hour.

In still a further variant of the cigar humidor, the germicidal light assembly is positioned on a bottom of the hollow housing, and the humidor includes a panel to serve as a floor of the humidor, the panel having a cutout to permit the germicidal light to shine into the interior of the housing. The panel with the cutout functions as a false floor in the humor and hides electronics and circuitry from then normal view of a user.

In another variant, a cigar humidor comprises: a hollow housing; a lid connected to the housing; a germicidal light assembly positioned inside the housing for disinfecting cigars; a platform transparent to ultraviolet light produced by the assembly; a hydrometer; a humidifier; a mirror positioned against an inside surface of the lid configured to face inside the hollow housing of the humidor when the lid is closed, wherein the mirror is configured to reflect light emitted by the germicidal light assembly, toward cigars placed on the platform; and a controller in electrical communication with the germicidal light assembly and configured to turn on and off the germicidal light assembly based on either a predetermined time sequence or a temperature feedback system.

In a variant of the cigar humidor, the germicidal light assembly is positioned on a bottom of the hollow housing, and the humidor includes a panel to serve as a floor of the humidor, the panel having a cutout to permit the germicidal light to shine into the interior of the housing. The panel has a cutout that functions as a false floor in the humor and hides electronics from then normal view of a user.

Other features and aspects of the invention will become apparent from the following detailed description, taken in conjunction with the accompanying drawings, which illustrate, by way of example, the features in accordance with embodiments of the invention. The summary is not intended to limit the scope of the invention, which is defined solely by the claims attached hereto.

BRIEF DESCRIPTION OF THE DRAWINGS

The present invention, in accordance with one or more various embodiments, is described in detail with reference to the following figures. The drawings are provided for purposes of illustration only and merely depict typical or example embodiments of the invention. These drawings are provided to facilitate the reader's understanding of the invention and shall not be considered limiting of the breadth, scope, or applicability of the invention. It should be noted that for clarity and ease of illustration these drawings are not necessarily made to scale.

Some of the figures included herein illustrate various embodiments of the invention from different viewing angles. Although the accompanying descriptive text may refer to such views as "top," "bottom" or "side" views, such references are merely descriptive and do not imply or require that the invention be implemented or used in a particular spatial orientation unless explicitly stated otherwise.

Figure 1:
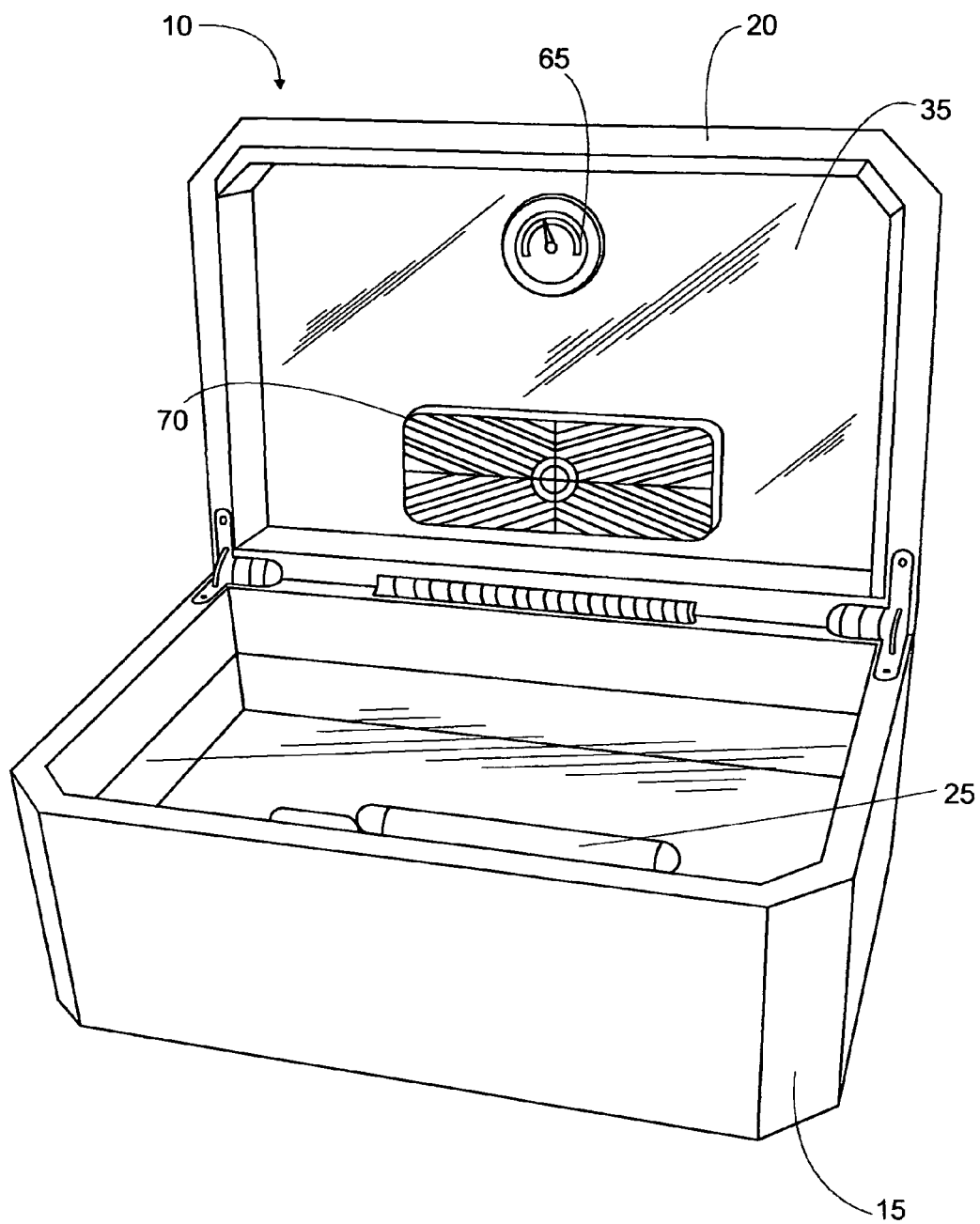
FIGS. 1-3 are perspective views of the cigar humidifier.

The figures are not intended to be exhaustive or to limit the invention to the precise form disclosed. It should be understood that the invention can be practiced with modification and alteration, and that the invention be limited only by the claims and the equivalents thereof.

DETAILED DESCRIPTION OF THE EMBODIMENTS OF THE INVENTION

From time-to-time, the present invention is described herein in terms of example environments. Description in terms of these environments is provided to allow the various features and embodiments of the invention to be portrayed in the context of an exemplary application. After reading this description, it will become apparent to one of ordinary skill in the art how the invention can be implemented in different and alternative environments.

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in applications, published applications and other publications that are herein incorporated by reference, the definition set forth in this document prevails over the definition that is incorporated herein by reference.

The following reference numbers are used in this document:
humidor 10
hollow housing 15
lid 20
germicidal light assembly 25
transparent platform 30 minor 35
temperature sensor 40
controller 45
bottom 50
panel 55
cutout 60
hydrometer 65
humidifier 70

Figure 2:
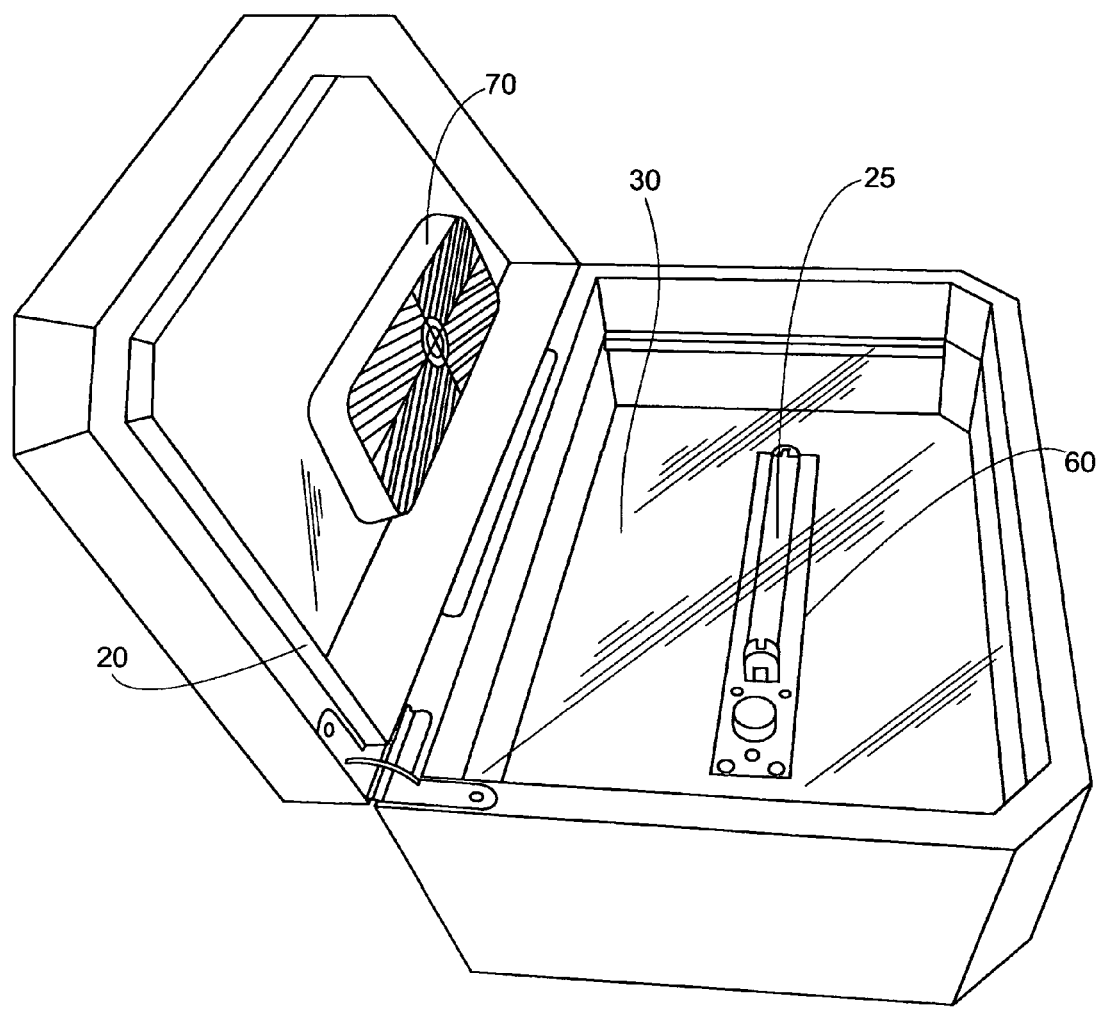
Figure 3:
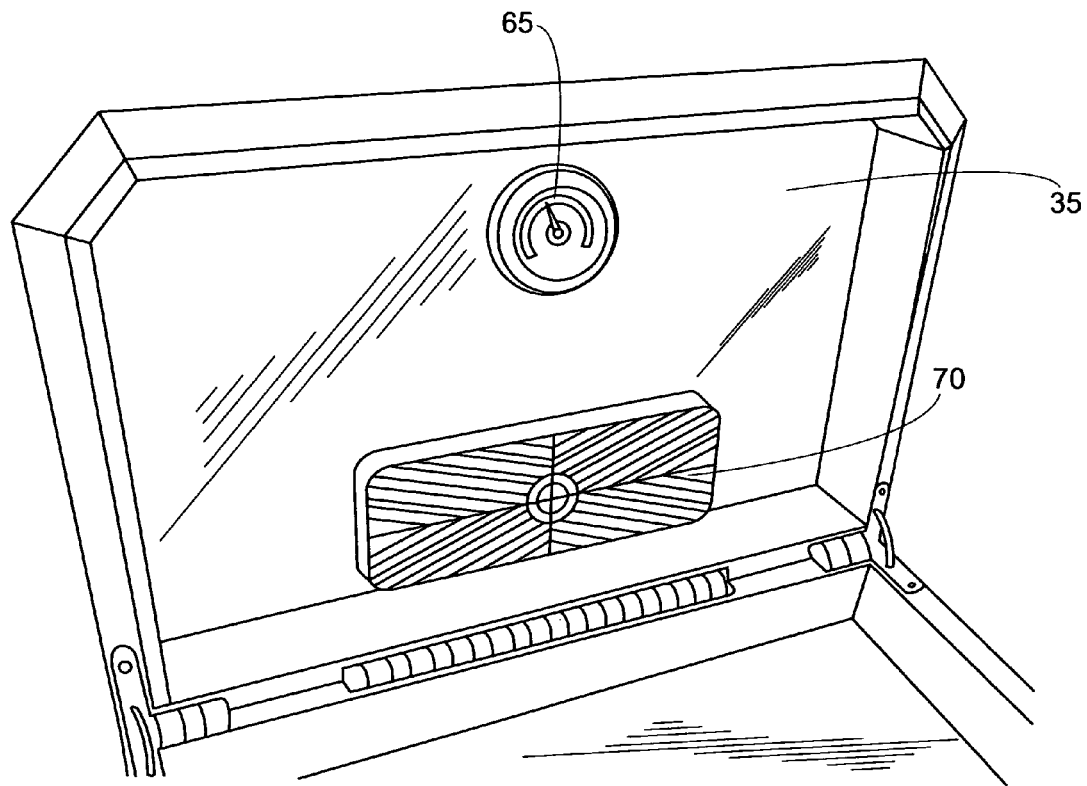
Figure 4:
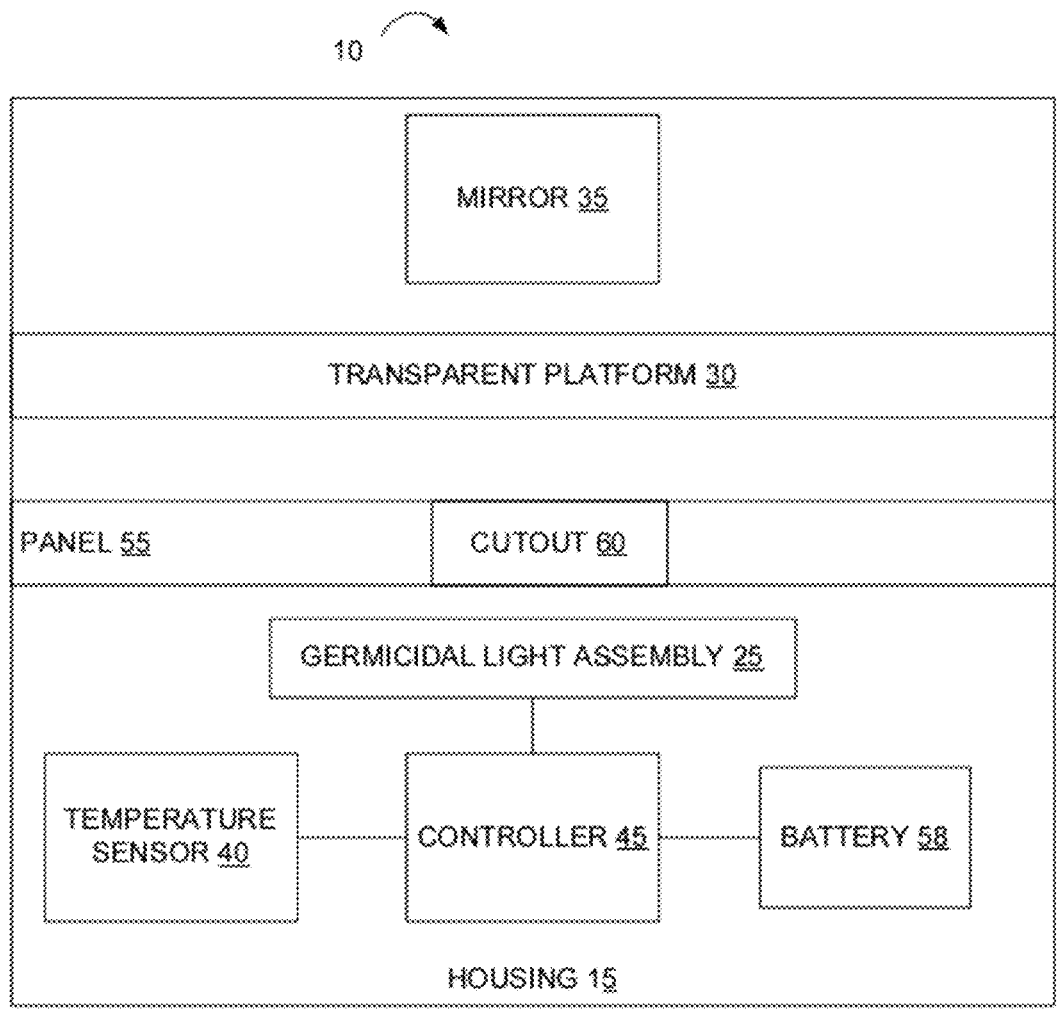
FIG. 4 is a block diagram of the cigar humidifier.

The present invention, in some embodiments thereof, relates to a cigar humidor 10. Referring to FIGS. 1-4, the humidor 10 comprises a hollow housing 15 and a lid 20 connected to the housing 15. A germicidal light assembly 25 is positioned inside the housing 15 for disinfecting cigars. A platform 30 is disposed inside the housing and is transparent to ultraviolet light produced by the assembly. A hydrometer 65 and a humidifier 70 may be disposed inside the humidifier and in one example is attached to the inside of the lid 20.

A germicidal light assembly 25 may be an ultraviolet germicidal lamp. One example light 25 may be an instant starting having a coil filament, for instance, the Ster-L-Ray™ Slimline Ultraviolet Germicidal Lamp produced by Atlantic Ultraviolet Corporation.

In a variant, the cigar humidor has a minor 35 positioned against an inside surface of the lid and the mirror is configured to face inside the hollow housing of the humidor when the lid 20 is closed. The mirror 35 is configured to reflect light emitted by the germicidal light assembly, toward cigars placed on the platform 30.

In another variant the cigar humidor includes a temperature sensor 40 configured to measure the air temperature inside the humidor and a controller 45 in electrical communication with the temperature sensor and configured to operate the germicidal light assembly according to a predetermined temperature set point. For example, the controller may be configured to read the temperature reading provided by the temperature sensor. If the temperature exceeds 68 degrees, the controller shuts off the light assembly. If the temperature falls below 68 degrees, the controller turns the light assembly on.

In a further variant of the cigar humidor, the controller 40 is configured to operate the germicidal light assembly according to a predetermined time sequence. In yet another variant, the predetermined time sequence comprises a repeating cycle of operating the light on for two hours followed by shutting off the light for one hour.

In still a further variant of the cigar humidor, the germicidal light assembly is positioned on a bottom 50 of the hollow housing, and the humidor includes a panel 55 to serve as a floor of the humidor, the panel having a cutout 60 to permit the germicidal light to shine into the interior of the housing. The panel with the cutout functions as a false floor in the humor and hides electronics and circuitry from then normal view of a user. For example, the controller and temperature sensor may be placed under the panel 55.

While various embodiments of the present invention have been described above, it should be understood that they have been presented by way of example only, and not of limitation Likewise, the various diagrams may depict an example architectural or other configuration for the invention, which is done to aid in understanding the features and functionality that can be included in the invention. The invention is not restricted to the illustrated example architectures or configurations, but the desired features can be implemented using a variety of alternative architectures and configurations. Indeed, it will be apparent to one of skill in the art how alternative functional, logical or physical partitioning and configurations can be implemented to implement the desired features of the present invention. Also, a multitude of different constituent module names other than those depicted herein can be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Although the invention is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the invention, whether or not such embodiments are described and whether or not such features are presented as being a part of a described embodiment. Thus the breadth and scope of the present invention should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

A group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise. Furthermore, although items, elements or components of the invention may be described or claimed in the singular, the plural is contemplated to be within the scope thereof unless limitation to the singular is explicitly stated.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, can be combined in a single package or separately maintained and can further be distributed across multiple locations.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

What is claimed is:

1. A cigar humidor, comprising:
   a hollow housing;
   a lid connected to the housing;
   a germicidal light assembly positioned inside the housing for disinfecting cigars;
   a platform transparent to ultraviolet light produced by the assembly;
   a mirror positioned against an inside surface of the lid configured to face inside the hollow housing of the humidor when the lid is closed, wherein the mirror is configured to reflect light emitted by the germicidal light assembly, toward cigars placed on the platform;
   a temperature sensor configured to measure the air temperature inside the humidor; and
   a controller in electrical communication with the temperature sensor and configured to operate the germicidal light assembly according to a predetermined temperature set point.

2. The cigar humidor of claim 1, wherein the controller is configured to operate the germicidal light assembly according to a predetermined time sequence.

3. The cigar humidor of claim 2, wherein the predetermined time sequence comprises a repeating cycle of operating the light on for two hours followed by shutting off the light for one hour.

4. A cigar humidor, comprising:
   a hollow housing;
   a lid connected to the housing;
   a germicidal light assembly positioned inside the housing for disinfecting cigars;
   a platform transparent to ultraviolet light produced by the assembly;
   a hydrometer; and
   a humidifier.

5. A cigar humidor, comprising:
   a hollow housing;
   a lid connected to the housing;
   a germicidal light assembly positioned inside the housing for disinfecting cigars;
   a platform transparent to ultraviolet light produced by the assembly;
   a hydrometer;
   a humidifier;
   a mirror positioned against an inside surface of the lid configured to face inside the hollow housing of the humidor when the lid is closed, wherein the mirror is configured to reflect light emitted by the germicidal light assembly, toward cigars placed on the platform; and
   a controller in electrical communication with the germicidal light assembly and configured to turn on and off the germicidal light assembly based on either a predetermined time sequence or a temperature feedback system.

6. The cigar humidor of claim 5, wherein the germicidal light assembly is positioned on a bottom of the hollow housing, and the humidor includes a panel to serve as a floor of the humidor, the panel having a cutout to permit the germicidal light to shine into the interior of the housing;
   wherein the panel having a cutout functions as a false floor in the humor and hides electronics from then normal view of a user.

* * * * *